(12) United States Patent
Thorwirth et al.

(10) Patent No.: US 6,542,241 B1
(45) Date of Patent: Apr. 1, 2003

(54) ARRANGEMENT FOR OPTICALLY READING OUT THE INFORMATION FROM SUBSTRATES HAVING A MULTIPLICITY OF INDIVIDUAL SAMPLES

(75) Inventors: Guenter Thorwirth, Laasdorf (DE); Werner Reiland, Cospeda Stadt Jena (DE)

(73) Assignee: Jena-Optronik GmbH, Jena (DE)

( * ) Notice: Subject to any disclaimer, the term of this patent is extended or adjusted under 35 U.S.C. 154(b) by 0 days.

(21) Appl. No.: 09/518,295

(22) Filed: Mar. 3, 2000

(30) Foreign Application Priority Data

Mar. 25, 1999 (DE) .......................................... 199 14 279

(51) Int. Cl.[7] .............................................. G01N 21/59
(52) U.S. Cl. ...................................... 356/436; 356/440
(58) Field of Search ................................... 356/436, 440

(56) References Cited

U.S. PATENT DOCUMENTS 4,004,150 A * 1/1977 Natelson ...................... 356/434
4,256,405 A * 3/1981 Fjarlie ........................... 356/454

FOREIGN PATENT DOCUMENTS

| DE | 44 23 802 A1 | 1/1996 |
| DE | 689 27 634 T2 | 5/1997 |
| DE | 197 36 641 A1 | 3/1999 |
| WO | WO 97/45730 | 12/1997 |

OTHER PUBLICATIONS

English Abstract of DE 689 27 634 T2.
English Abstract of DE 197 36 641 A1.
English Abstract of DE 44 23 802 A1.

* cited by examiner

Primary Examiner—Richard A. Rosenberger
(74) Attorney, Agent, or Firm—Reed Smith LLP

(57) ABSTRACT

An arrangement is disclosed for optically reading out the information from substrates having a multiplicity of individual samples, in particular for analyzing chemical and biological sample carriers. The arrangement presents a new possibility for optically reading out the information from matrix-type substrates having a multiplicity of individual samples which allows a fast read-out of a radiation which is influenced by the individual samples with a high degree of sensitivity. This possibility is achieved by the fact that, in the case of optically reading a matrix-type substrate having a multiplicity of metrically ordered pixels, the receiver that is provided is an individual receiver which has high sensitivity and a uniform receiver area, an electrooptical matrix and also an imaging optical system are present, each substrate pixel being assigned to a matrix pixel region by the imaging optical system, and the matrix can be driven in such a way that matrix regions which allow exclusively the feeding of radiation from a substrate pixel to the receiver can be switched separately. Radiation quantities from in each case at least one substrate pixel successively impinging on the receiver over a suitably chosen time interval. The result is that it is possible to evaluate a series of measured radiation quantities from selected sequences of substrate pixels at the output of the receiver.

39 Claims, 8 Drawing Sheets

ARRANGEMENT FOR OPTICALLY READING OUT THE INFORMATION FROM SUBSTRATES HAVING A MULTIPLICITY OF INDIVIDUAL SAMPLES

BACKGROUND OF THE INVENTION a) Field of the Invention

For tasks appertaining to the biotechnical analysis (screening) of large quantities of samples, e.g. for genetic analysis (e.g. viral diagnosis), the use of so-called microtiter plates and associated manipulation technology (e.g. automatic machines for filling the individual cavities in the microtiter plate) is an established technology (pharmacological research, clinical practice etc.).

b) Description of the Related Art

This technology is distinguished by the fact that in a microtiter plate with a size of 8 cm×12 cm, depending on the embodiment, 96 (most common type), 384 or 1536 (probably the maximum possible value for microtiter plate technology with only minor application heretofore) different sample substances can be accommodated. In order to fill the individual cavities, sample quantities of the order of magnitude of 100 µl are necessary depending on the type of microtiter plate.

In the course of increasing the effectiveness, international research and development work is currently underway with the aim of significantly increasing the number of cavities (that can be processed in parallel) in conjunction with significantly reducing the required sample quantities and significantly increasing the sample throughput. These aims are intended to be achieved by the transition from microtiter plates to biochips (e.g. manufactured using microphotolithographic technologies) and fast read-out and processing (high throughput screening, HTS) of the biochips.

An individual biochip may comprise spots (comparable with the cavities in the microtiter plate) numbering tens of thousands on an area of a few $mm^2$ to $cm^2$, sample quantities of the order of magnitude of a few nanoliters being necessary altogether over all the spots.

In order to read biochips (and also microtiter plates or any other chemical sample carriers), the sample material is irradiated with light in the UV through to the NIR region, depending on the type of samples, and the influence on the radiation by the sample material (e.g. absorption) or the effect of the illumination radiation on the sample material (e.g. excitation of a luminescent radiation) is measured.

In order to read the matrix-type arrangement of the pixels on a biochip, the following two techniques are known in principle:

1. Serial illumination by means of a laser scanner and read-out of the individual sample images (pixels) of the sample carrier using a single optoelectronic photoreceiver, e.g. photon counter/secondary electron multiplier (SEM)/photo multiplier tube (PMT).

2. Parallel illumination and simultaneous read-out of many or all of the pixels of the sample carrier using an optoelectronic receiver matrix (e.g. CCD).

Reading units that have been disclosed for microtiter plates operate (due to the dimensions of these plates) practically exclusively according to the scan principle. In the case of this principle, the individual samples (cavities) of the sample carrier are each excited separately (successively in time). Laser scanners are used for this purpose because narrowband coherent laser radiation, in contrast to broadband incoherent radiation, can be focused without difficulty onto small pixel areas (a few $\mu m^2$).

The narrowband nature of the laser radiation used is advantageous, on the one hand, since narrowband excitation is necessary in order to excite a specific marker (e.g. fluorescent marker) in a targeted manner, which is disadvantageous on the other hand, if different excitation wavelengths are required for different markers and it is thus necessary to change the laser light source (or use cost-intensive tunable lasers).

In the case of the camera principle, it is fundamentally possible also to use cost-effective broadband (thermal) light sources for the illumination, with the result that only one excitation filter has to be exchanged when the marker is changed. Using broadband light sources is expedient for a host of applications, which speaks in favor of the use of the camera principle for cost reasons.

One example of the application of the camera principle is a nanotiter plate read-out unit described in the technical paper "Optische Mikrosysteme für die Umweltmeßtechnik" [Optical microsystems for environmental metrology] (in: Laser und Optoelektronik, 30(1), 1998, pp. 33–35).

On the other hand, the scan principle is recommended on account of the use of highly sensitive SEMs, which results, in particular, in especially good detection sensitivity in the case of weak secondary radiation, which is regularly absent from the camera principle owing to the less sensitive matrix receivers used and has to be compensated for by relatively long integration times (a few tens of seconds through to a few minutes) and the use of costly cooled receiver matrices (for largely suppressing the generation of thermal charge carriers during the integration time).

From this standpoint there have also been endeavors to combine a broadband radiation source with a sensitive SEM as radiation receiver in a measuring apparatus which has been disclosed, in terms of equipment engineering, as an ultrahigh throughput screening system (from Carl Zeiss Jena GmbH) for processing 96-type microtiter plates with 96 optical transmission channels and an SEM for each channel. However, this solution leads to very high costs and seems inconceivable for pixel numbers of the order of magnitude of several thousands to tens of thousands of pixels.

The invention is based on the object of finding a new possibility for optically reading out the information from matrix-type substrates having a multiplicity of individual samples which allows a fast read-out of a radiation which is characteristically influenced by the individual sample substances with a high degree of sensitivity. In addition, the intention is to find a possible way of departing from the storage of a complete (image) file of the local distribution of the radiation intensities on the matrix-type substrate and, for specific objectives (e.g. comparison of the present radiation distribution with a catalog of possible distributions), of performing, as early as in the optical channel, a suitably adaptable data reduction or an initial evaluation situated upstream (with respect to the subsequent digital evaluation by means of a PC or the like).

The object is achieved according to the invention, in the case of an arrangement for optically reading out the information from a matrix-type substrate having a multiplicity of individual samples, which represent metrically ordered pixels on the substrate and emit a radiation which is characteristically influenced by the respective sample substance, having a transfer optical arrangement for separately transferring the radiation emitted by individual substrate pixels to a receiver, by virtue of the fact that the receiver is an individual receiver which has high sensitivity and a uniform receiver area and is able to take up the radiation from each substrate pixel, that the transfer optical arrangement has an electrooptical matrix, which has the function of a variable light valve for separately transferring radiation from each substrate pixel to the receiver, and also an imaging optical system, each substrate pixel being assigned to a matrix region, comprising at least one matrix pixel, by means of the imaging optical system, and that the matrix can be driven in such a way that matrix regions of such a size which allow exclusively the feeding of radiation from a substrate pixel to the receiver can be switched separately, radiation quantities from in each case at least one substrate pixel successively impinging on the receiver over a suitably chosen time interval, with the result that it is possible to evaluate a series of measured radiation quantities from selected sequences of substrate pixels at the output of the receiver.

Intensive illumination is preferably provided for generating the radiation which is characteristically influenced by the substrate pixels. This illumination is expediently chosen such that the substrate pixels emit a luminescent radiation, preferably a fluorescent radiation, which is generated by the illumination. Furthermore, the illumination may expediently be used for reading out the transmissivity or reflectivity as the characteristically influenced radiation from the substrate pixels. For the illumination, provision may advantageously be made of an illumination device having a parallel pencil of rays which, with optical components arranged downstream being taken into account, is suitable for the large-area uniform illumination of all the substrate pixels.

Another suitable possibility for generating the radiation which is characteristically influenced by the substrate pixels is afforded by causing a chemical reaction in a targeted manner by contact of the substrate pixels with a surrounding medium, preferably with a liquid. In this case, too, the luminescent radiation excited by an energy input will be detectable.

For all of the aforementioned cases of generating radiation from the substrate pixels to be evaluated, it is advantageous, in the arrangement according to the invention, that the transfer optical arrangement is arranged between the substrate and the receiver, it being possible for the characteristic radiation from each substrate pixel to be detected individually on the receiver by assigned matrix regions of the electrooptical matrix being switched to be transparent.

In this case, each substrate pixel is expediently imaged by means of the imaging optical system on a respective matrix pixel, it being possible in each case for the characteristic radiation from the assigned substrate pixel to be detected on the receiver by an arbitrary matrix pixel being switched to be transparent. In many cases, however, when the imaging scale is altered, it proves to be favorable if each substrate pixel is imaged by means of the imaging optical system on a respective group of matrix pixels which is geometrically similar to the area of the substrate pixels, it being possible likewise for only the characteristic radiation from an assigned substrate pixel to be detected on the receiver by such a group of matrix pixels being switched to be transparent.

In another advantageous variant, the transfer optical arrangement is arranged upstream of the substrate in the parallel pencil of rays from the illumination device, the matrix pixels of the electrooptical matrix being illuminated uniformly by the illumination device and it being possible for the substrate pixels to be illuminated individually with the illumination light by activation of defined matrix regions of the electrooptical matrix, and the substrate being connected to the receiver in such a way that the radiation coming from any arbitrary substrate pixel can be taken up by means of the receiver essentially without any losses. In this case, a respective matrix pixel is imaged by means of the imaging optical system on a substrate pixel, the assigned substrate pixel, for generating the characteristic radiation, being illuminated by activation of the respective matrix pixel. In this case, too, it may be expedient for the abovementioned reasons for a respective group of matrix pixels which is geometrically similar to the substrate pixels to be imaged by means of the imaging optical system on a substrate pixel in order once again to illuminate the assigned substrate pixel by activation of respective group of matrix pixels.

The electrooptical matrix that is provided is expediently a ferroelectric-based liquid crystal matrix (that is to say an LC matrix having bistable switching states, high contrast and short switching times). However, it is also possible to use any other arbitrary liquid crystal matrices having a high contrast ratio between the transparent and nontransparent states, if they have a sufficiently high switching speed.

In addition to the imaging optical arrangements normally used, it is also advantageously possible to use fiber optical arrangements, preferably a fiber plate, as the imaging optical system, a light-guiding connection being established between the substrate pixels and the assigned matrix pixels as a result of direct contact of the fiber optical arrangement with the substrate, on the one hand, and the electrooptical matrix, on the other hand, in order to avoid losses of light due to scattering effects in the air. Depending on the embodiment of the invention, any arbitrary beam-guiding optical elements (e.g. microchannel plate, image-guiding cable with or without fiber taper) or imaging optical elements (e.g. lenses, lens arrays or the like) can be used for all the transfer paths of the radiation from the substrate pixels (both between the substrate and the switchable matrix and between the switchable matrix and the receiver and the substrate and the receiver).

Furthermore, the arrangement according to the invention affords diverse possibilities for optical data reduction. For this purpose, the electrooptical matrix can advantageously be activated in suitably chosen matrix regions, with the result that radiation quantities from a plurality of selected substrate pixels can be detected simultaneously on the receiver and are combined (integrated) to form a receiver measured value, it being possible to compare measured values that have been obtained in this way with radiation values of specimen substrates which have been measured under the same preconditions. Real-time comparison of integrated measured values with a specimen database is thus possible without complicated (image) data evaluation of all the substrate pixels. Likewise, the integral treatment of the entire substrate means that certain exclusion analyses can be carried out, e.g. whether a specific substance is actually present in any of the substrate pixels. For the cases of reading out the substrate pixels based on luminescence (or specifically fluorescence) generated by an energy input, the illumination device advantageously contains an incoherent light source and a narrowband excitation filter tuned to the excitation wavelength of the luminescent material of the substrate pixels. The excitation filter can expediently be exchanged for adaptation to different luminescent materials. For this reason, in particular, the illumination device has a relatively broadband powerful light source. Any arbitrary commercially available radiators from halogen lamps through mercury vapor lamps, xenon lamps to powerful light-emitting diodes can be used as suitable light sources. In principle, there is also no obstacle to using a coherent light source (laser) provided with beam-expanding optics for the proper functioning of the arrangement according to the invention, if the wavelength of the laser is adapted to the excitation wavelength of the luminescent materials of the substrate pixels or a tunable laser is used. This is detrimental, however, to the costs and to overcoming the limitations known in the prior art when any arbitrary luminescent materials are used.

With regard to its geometrical arrangement, the illumination device may advantageously be configured in different variants. It is designed in a transmitted-light bright-field configuration in particular for evaluations of the transmission of the substrate pixels. Reflected-light dark-field and transmitted-light dark-field configurations are particularly advantageous for luminescence excitation but can likewise be used in measurements of the transmissivity and reflectivity of the substrate pixels. In order to increase the efficiency of the luminescence excitation, the two dark-field configurations can expediently be combined by arranging a mirror in the light path of the parallel pencil of rays which transmissively passes through the substrate, the reflected light of which mirror falls onto the substrate again as an additional reflected-light dark-field light pencil.

If the electrooptical matrix is used—as described above—in the illumination beam path for the purpose of controlling the successively separate illumination of the individual substrate pixels, a reflected-light dark-field configuration is likewise expedient, in which case the activation of the matrix pixels must then result in a change to their reflectivity. In all the variants of the invention which operate with illumination of the substrate pixels, a rejection filter for eliminating the illumination light is expediently arranged in the beam path upstream of the receiver, in particular for the evaluation of the excited luminescent radiation.

Owing to the mainly very weak radiation from the substrate pixels, a secondary electron multiplier (SEM/PMT) is advantageously used as the individual receiver. Radiation-concentrating optical elements which concentrate (focus) the characteristically influenced radiation from all the substrate pixels onto the active light-sensitive area of the receiver are expediently provided upstream of the receiver, if the light-sensitive area of the individual receiver is smaller than the area of the substrate to be read or of the upstream electrooptical matrix. For this purpose, a converging optical arrangement, a lens array or a radiation-concentrating cross-section converter are preferably inserted upstream of the receiver. Said converter may be e.g. a truncated glass cone.

In order to configure the arrangement according to the invention such that it is robust in the face of thermal and other environmental influences (such as, for example, vibrations in the course of mobile operations), an electromechanical actuating unit is advantageously provided for regularly readjusting the transfer optical arrangement relative to the substrate. For this purpose, it may be beneficial, on the one hand, for the substrate to be able to be displaced two-dimensionally, by means of the actuating unit, relative to the entire transfer optical arrangement in an orthogonal plane with respect to the optical axis and to be able to be rotated at least about one axis (preferably that of the longest extent of the substrate). On the other hand, it is virtually equivalent, but more convenient, to configure the electrooptical matrix such that it can be displaced, by means of the actuating unit, relative to the imaging optical system and the substrate in two directions of an orthogonal plane with respect to the optical axis and can be rotated at least about one axis.

The mechanical actuating unit that is used is advantageously a piezoelectric x,y,Φ actuator whose driving and regulation are based on maximizing the luminescent light efficiency for defined substrate pixels, in particular edge pixels, of a specimen substrate.

The fundamental idea behind the invention is based on the consideration that an arrangement for reading matrix-type substrates having a multiplicity of individual samples (in particular biochips having up to ten thousand spots) should have a broadband light source for parallel illumination of all the pixels, in order to achieve uniform illumination as far as possible of all the substrate pixels, with the result that the latter can be read out arbitrarily (independently of the concrete read-out regime) at short time intervals, and should contain an optoelectronic individual receiver (e.g. SEM) which ensures sufficient read-out sensitivity even when the intensity of the radiation is low (e.g. luminescent radiation or low degree of transmission in the case of transmitted-light illumination).

The contradiction which arises in the case of the technical realization on account of the relatively small, non-spatially-resolving receiver area of an SEM when the entire substrate is imaged is resolved by a matrix-type light shutter arrangement being arranged upstream of the receiver, in the case of which the number of matrix elements corresponds to the number of substrate pixels and said matrix elements can be switched separately in terms of their light transmission or reflection with a high contrast ratio, with the result that the radiation from each substrate pixel which is characteristically influenced (by the sample substance) can be detected separately on the receiver. In addition, it is possible to permit combination (of not necessarily contiguous) regions in the image of the substrate (e.g. for real-time evaluation in the exclusion process using specimen databases).

The invention will be described in more detail below using exemplary embodiments.

DESCRIPTION OF THE PREFERRED EMBODIMENTS

Figure 1:
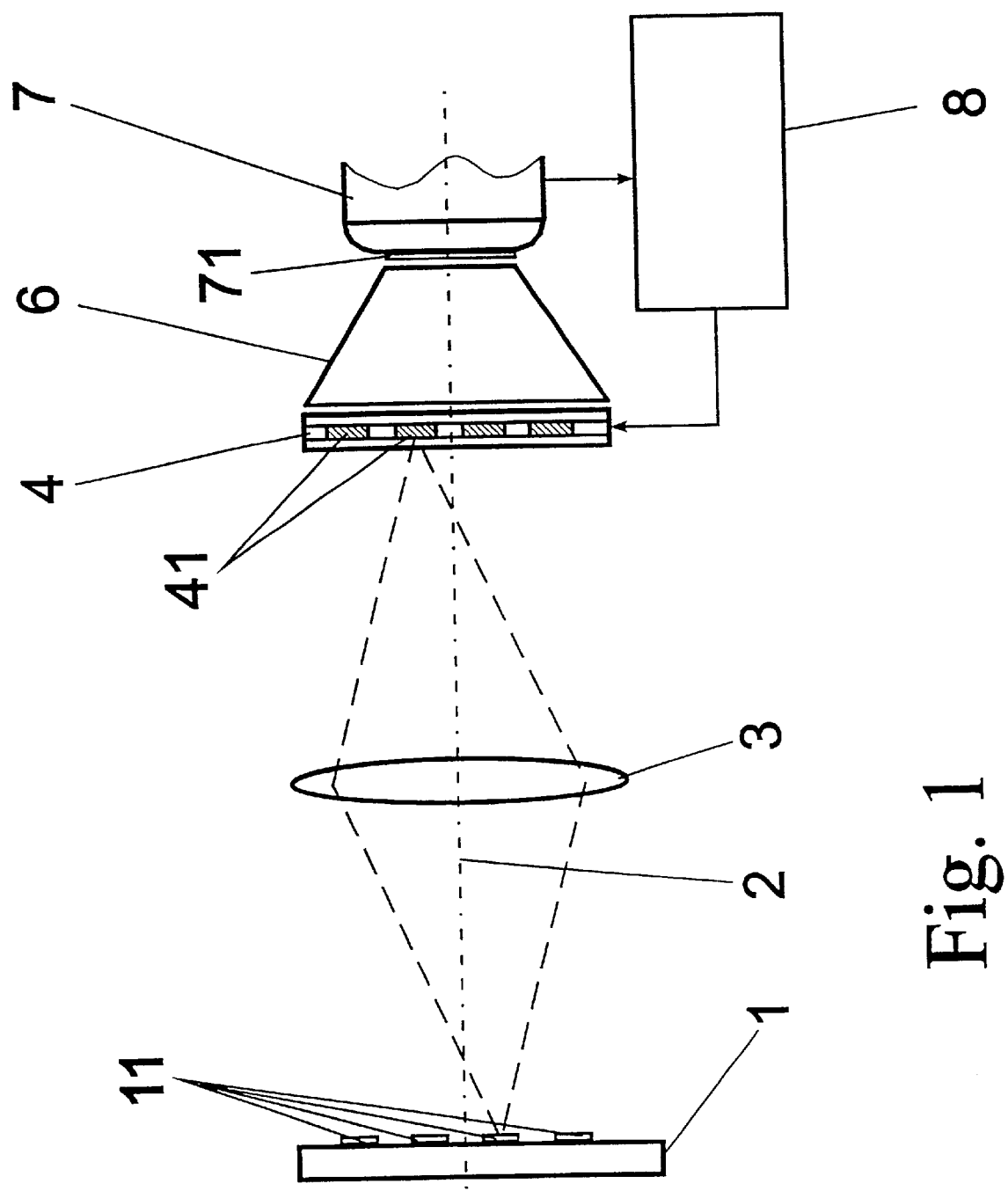
FIG. 1 shows the fundamental structure of the arrangement according to the invention.

In terms of its fundamental structure—as illustrated in FIG. 1—the arrangement according to the invention comprises a matrix-type substrate 1 having a multiplicity of individual samples which represent metrically ordered substrate pixels 11 on the substrate 1 and emit a radiation which is characteristically influenced by the respective sample substance, the substrate 1 being followed, for the purpose of optical read-out, on a common optical axis 2, by a transfer optical arrangement, comprising an imaging optical system 3 and an electrooptical matrix 4, and by the receiver 7 with an upstream radiation-concentrating element 6 for focusing all the radiation from the substrate pixels 11 which is transferred via the matrix 4. In this case, an evaluation unit 8 controls the read-out regime by means of the matrix 4 and registers the optoelectronically converted radiation quantities of the substrate pixel radiation taken up by the receiver 7.

The radiation from the substrate pixels 11 which is characteristically influenced in a substance-inherent manner can be triggered in different ways, but a triggering event which feeds energy to the substrate pixels is necessary in each case. That will most often be intensive illumination, but may also happen as a result of energy liberated from a chemical reaction upon contact with a surrounding medium. For the latter case, the arrangement illustrated would thus already be functional and could be changed, if appropriate, only by variations to the imaging and radiation-concentrating optical elements in order to achieve more compact designs or configurations for specific applications, as described further below.

As indicated by the dashed line in FIG. 1, there is an unambiguous imaging assignment between the substrate pixels 11 and the pixels 41 of the electrooptical matrix 4. That is necessary because, according to the invention, the matrix 4 is used as a light valve which operates in a spatially differentiated manner, in order to transfer the radiation from each individual substrate pixel 11 separately to the light-sensitive area 71 of the receiver 7.

Various designs of the invention with the radiation from the substrate pixels 11 being generated by illumination are discussed in the text below. All modifications of the arrangement as shown in FIG. 1 which are not specifically related to the configuration of the illumination device 9 can likewise be applied to said arrangement and should thus also be interpreted as referring back thereto.

Figure 2:
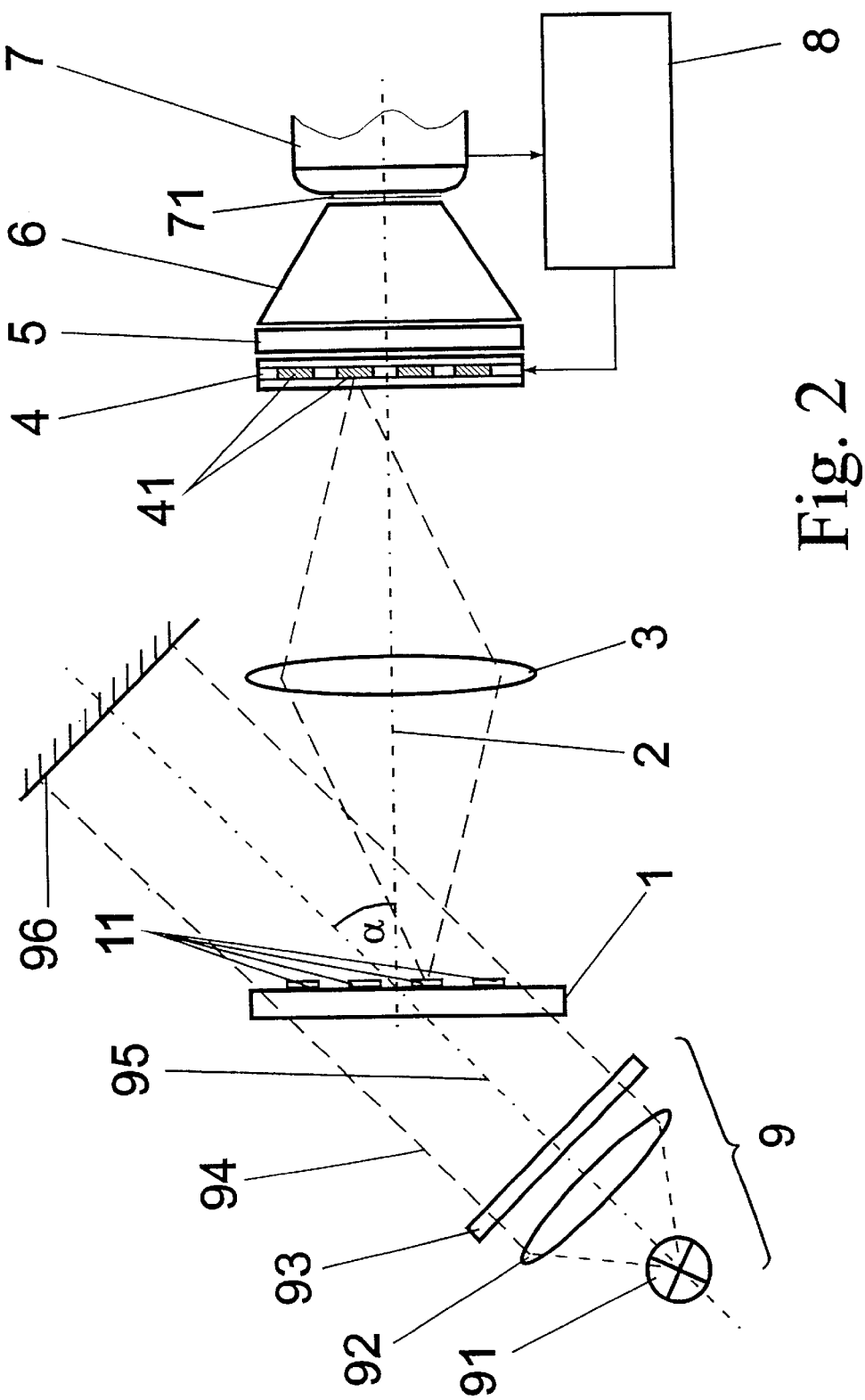
FIG. 2 shows a configuration of the invention with excitation of the substrate pixels by combined dark-field illumination.

FIG. 2 illustrates an illumination device 9 in a configuration according to the dark-field method. In other words, the optical axis 95 of the incident illumination forms an angle a with the optical axis 2, on which the substrate 1, the imaging optical system 3, the matrix 4 and the receiver 7 are arranged, under which angle a all of the substrate pixels 11 are illuminated. The illumination device 9 contains a broad-band incoherent radiation source 91 (e.g. a halogen lamp, a xenon lamp, a mercury vapor lamp, a light-intense light-emitting diode or an array of not necessarily identical LEDs). The radiation cone proceeding from the light source 91 is guided via a condenser optical arrangement 92 and a narrowband excitation filter 93 as a parallel light pencil 94 through the transparent substrate 1 (e.g. biochip, micro-preparation carrier made of glass or the like) onto the substance of the substrate pixels 11 which is to be excited. In this case, the excitation filter 93 is tuned to the excitation wavelength of the substance that can be excited in the substrate pixels 11, and can be exchanged as required.

A substantial part of the collimated (parallel) pencil 94 of rays will pass through the substrate pixels 11. By the use of a mirror 96 perpendicular to the optical axis 95 of the illumination device 9, the parallel pencil 94 of rays is once again guided onto the substrate 1 in the form of a reflected-light dark-field method and thereby increases the excitation intensity that can effectively be utilized for the excitation (luminescence, in particular fluorescence).

Hereinafter, the excited radiation from the substrate pixels 11 will be assumed to be fluorescence, without restricting the generality.

Figure 7:
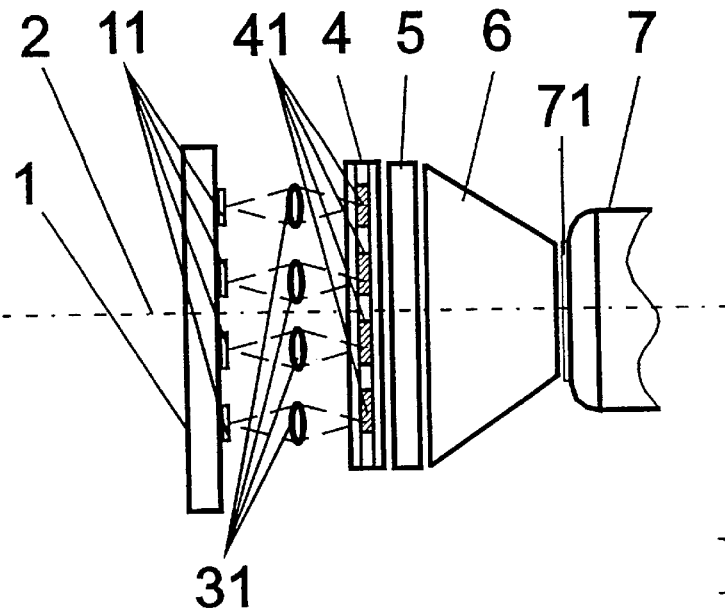
FIG. 7 shows a possible configuration of the imaging optical system between the substrate and the electrooptical matrix.

The fluorescent radiation excited in the substrate pixels 11 is imaged by means of the imaging optical system 3 (called objective 3 below) on the matrix pixels 41 of an electrooptical matrix 4, which will be designated below, in a simplified manner, as a liquid crystal matrix (LC matrix 4). The substrate pixels 11, objective 3 and matrix pixels 41 are arranged in this case in the beam path in such a way that the plane in which the substrate pixels 11 are situated is imaged in the plane in which the matrix pixels 41 of the LC matrix 4 are situated. In the case of this real imaging, each pixel 11 of the substrate 1 is assigned at least one matrix pixel 41. Expedient variants for the assignment of the substrate pixels 11 to the matrix pixels 41 include ratios of 1:4 or 1:9 as well as the 1:1 assignment. A favorable embodiment, because it is compact, can also be obtained by designing the objective 3 as a lens array comprising individual lenses 31 (as shown by a detail in accordance with FIG. 7). In this case, exactly one individual lens 31 of the lens array is provided for the optimum imaging of each substrate pixel 11 on the chosen number of assigned matrix pixels 41.

Figure 8:
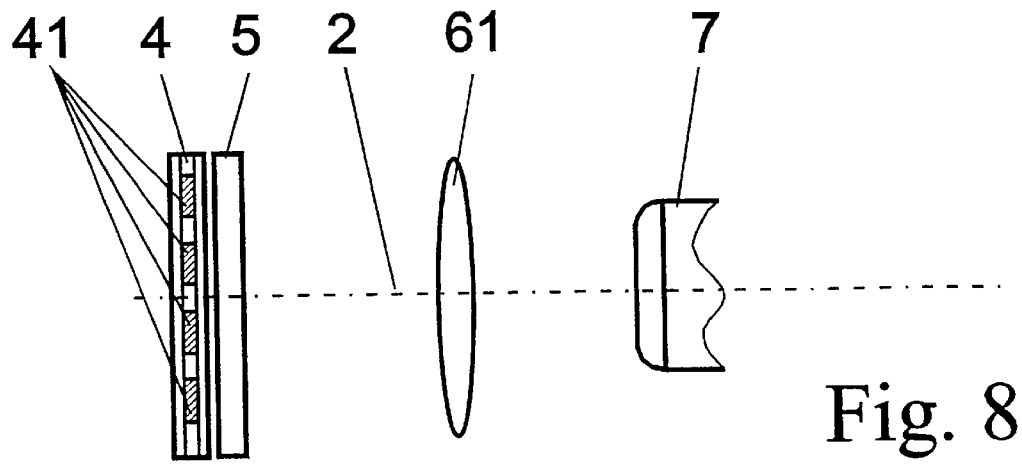
FIG. 8 shows an alternative possibility for the radiation-concentrating element shown in FIGS. 1 to 6.

A rejection filter 5 for eliminating the excitation radiation, a radiation-concentrating (focusing) optical element 6 and a (highly sensitive) optoelectronic secondary electron multiplier (SEM) as receiver 7 are arranged one after the other downstream of the LC matrix 4 in the beam propagation direction. The light-converging element 6 may be designed, as illustrated in FIGS. 2–6, as a two-dimensional cross-section converter (fiber taper bundle, monolithic truncated cone made of glass or the like). A converging lens 61 (see detail in accordance with FIG. 8) is likewise possible at this location. The light-converging element 6 is designed and arranged, irrespective of its technical realization, in principle in such a way that it concentrates (focuses) the entire fluorescent radiation which passes through the LC matrix 4 and the rejection filter 5 onto the light-sensitive area 71 of the receiver 7.

Figure 9:
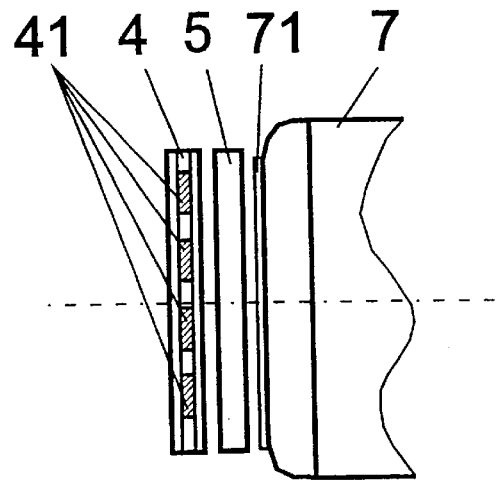
FIG. 9 shows the simplest variant of low-loss light coupling between the electrooptical matrix and the receiver.

In the case where the whole optically active area of the LC matrix 4 is not larger than the light-sensitive area of the receiver 7, the LC matrix 4, the rejection filter 5 and the receiver 7 can also be arranged directly (practically in contact) one after the other in the beam path, as is shown in FIG. 9. In this case, the light-converging element 6 is completely omitted. The order in which the LC matrix 4 and the rejection filter 5 are arranged in the optical beam path may also be interchanged.

In order to read the substrate 1, those matrix pixels 41 of the LC matrix 4 which correspond to the individual substrate pixels 11 are temporally successively switched to transmission and, for each of these switching states, the measured value of the receiver 7 is recorded in the evaluation unit 8 and stored, ordered according to the local position of the open switching state, and, if appropriate, already evaluated. The fluorescent radiation from each substrate pixel 11 is imaged exactly on one or on a defined number (e.g. 4 or 9) of switchable pixels 41 of the LC matrix 4.

Those matrix pixels 41 of the LC matrix 4 which are assigned exactly to one substrate pixel 11 are in each case opened successively in time. As a result, in each case only the radiation from one substrate pixel 11 successively reaches the entry window 71 as active area of the SEM 7 on the photocathode thereof, where it is converted into an electrical signal. The LC matrix 4 is expediently a ferroelectric-based liquid crystal matrix (that is to say an LC matrix 4 having bistable switching states, high contrast and short switching times).

For the driving of the LC matrix 4, different modes may be expedient depending on the objective formulated. A number of examples will be mentioned below.

The LC matrix 4 is driven in such a way that the measured values of the receiver 7 correspond exactly to the fluorescent intensity of the individual substrate pixels 11. In this case, only those matrix pixels 41 which correspond exactly to the imaged area of a substrate pixel 11 are ever switched to transmission at an arbitrary point in time. In this case, the measured values are recorded in chronological order as in the case of the so-called scan principle of the prior art.

In some cases it may suffice not to measure the fluorescent intensities of all the substrate pixels 11 in this way but rather to drive only a number of selected pixel coordinates of the electrically drivable LC matrix 4 and thus to measure, of the assigned substrate pixels 11, whether or not the expected fluorescence is present (exclusion method).

Furthermore, the LC matrix 4 can be driven in such a way that the fluorescent intensities of all or only selected substrate pixels 11 are either fed to the receiver successively in time and integrated upward (or summed) to form a measured value or (by the simultaneous opening of a plurality of assigned regions of matrix pixels 41) the fluorescent radiation from a plurality of substrate pixels 11 is taken up simultaneously. In this case, it is expedient, for example, to form measured values which are cumulative in a row-by-row, column-by-column or matrix-by-matrix manner and are compared with cumulative measured intensity values of a specimen substrate that have been learned beforehand in the same way. The number of such cumulative measured values that is necessary for unequivocally distinguishing (classifying) substrates 1 depends on a multiplicity of factors, in particular on the number of classes to be distinguished, the significance of their differences and the tolerance range of the optical properties given identical information of the substrates with a learned specimen substrate.

Information is obtained in an even more targeted manner by driving the LC matrix 4 in such a way that the fluorescent intensity of a predetermined quantity of substrate pixels 11 (defined number and coordinates on the substrate 1) is measured simultaneously. In this case, these predeterminable quantities of substrate pixels 11 can be chosen for example in such a way that they correspond to the fluorescent radiation patterns, stored beforehand in a library, of known biological substances (e.g. viruses or the like) (e.g. positive and/or negative radiation pattern). In this way, it is possible, for example, to assess a biochip to be read as the substrate 1 in the exclusion method, in which case a substantial part of the information processing (in the sense of information reduction) is already realized in the optical channel of the reading device and, consequently, real-time evaluation can be performed initially in the evaluation unit 8.

Figure 3:
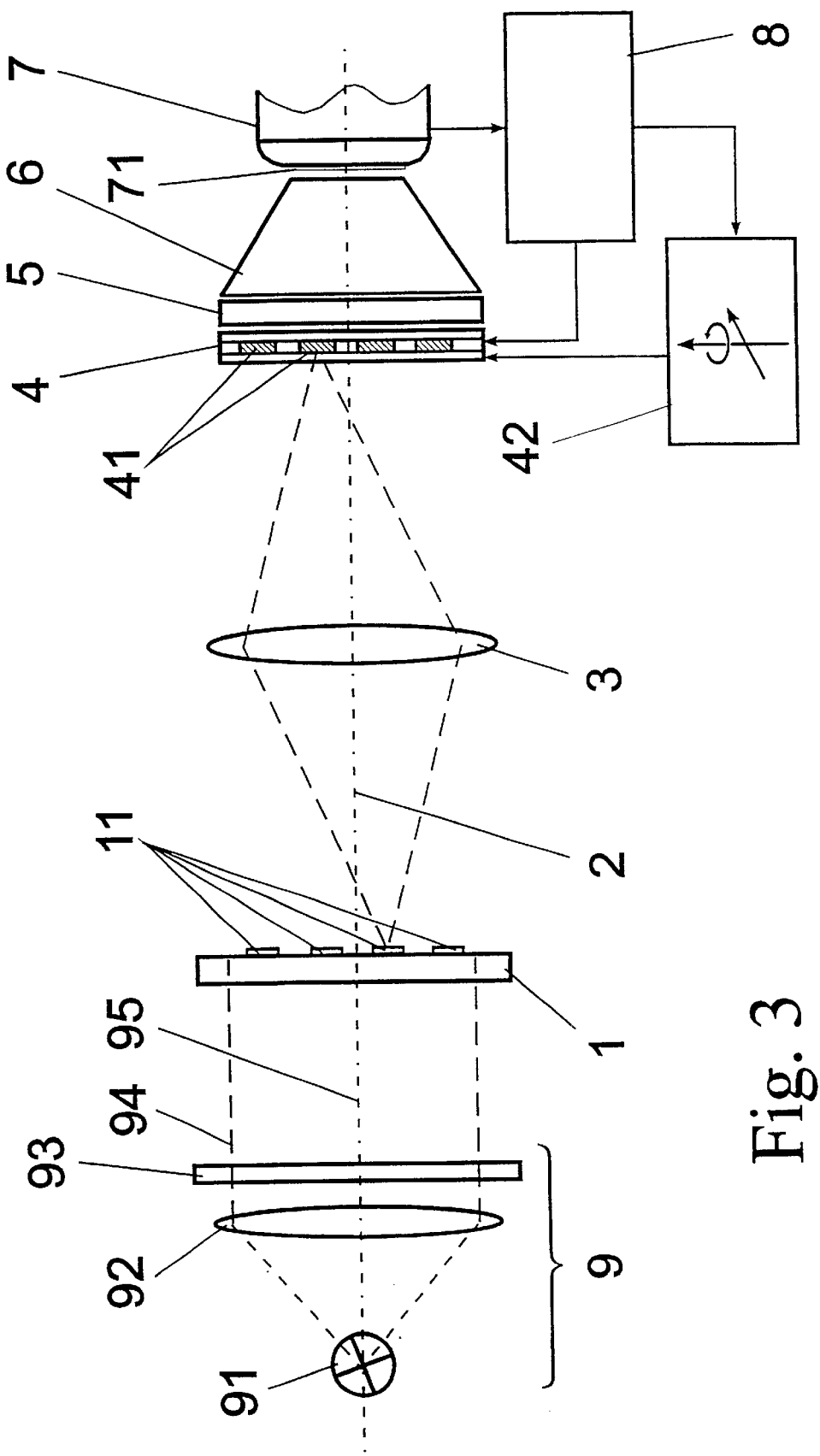
FIG. 3 shows transmitted-light bright-field illumination, preferably for luminescence excitation of the substrate pixels, which is also suitable for transmission measurements.
Figure 4:
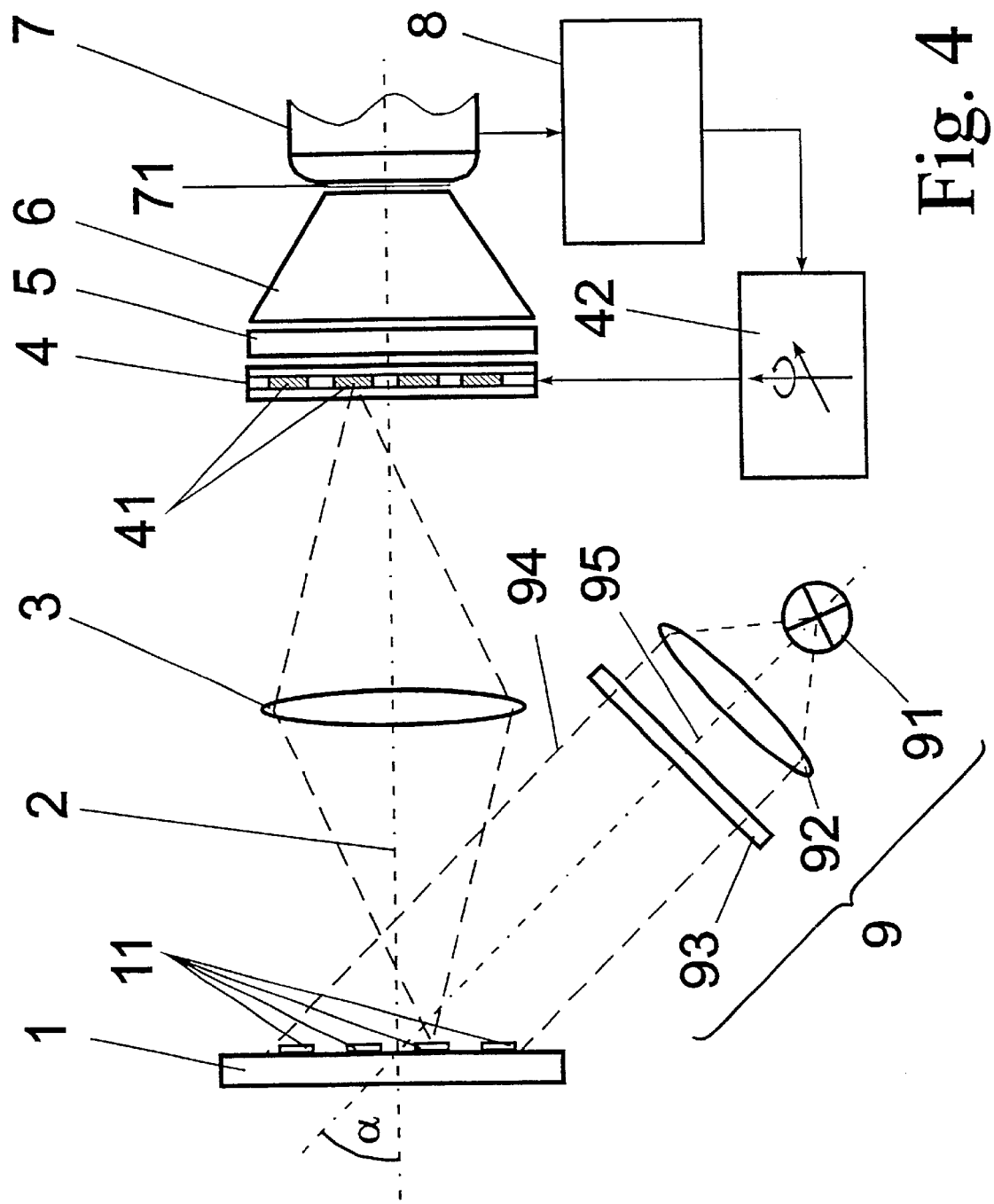
FIG. 4 shows an alternative configuration of the illumination based on FIG. 3.
Figure 5:
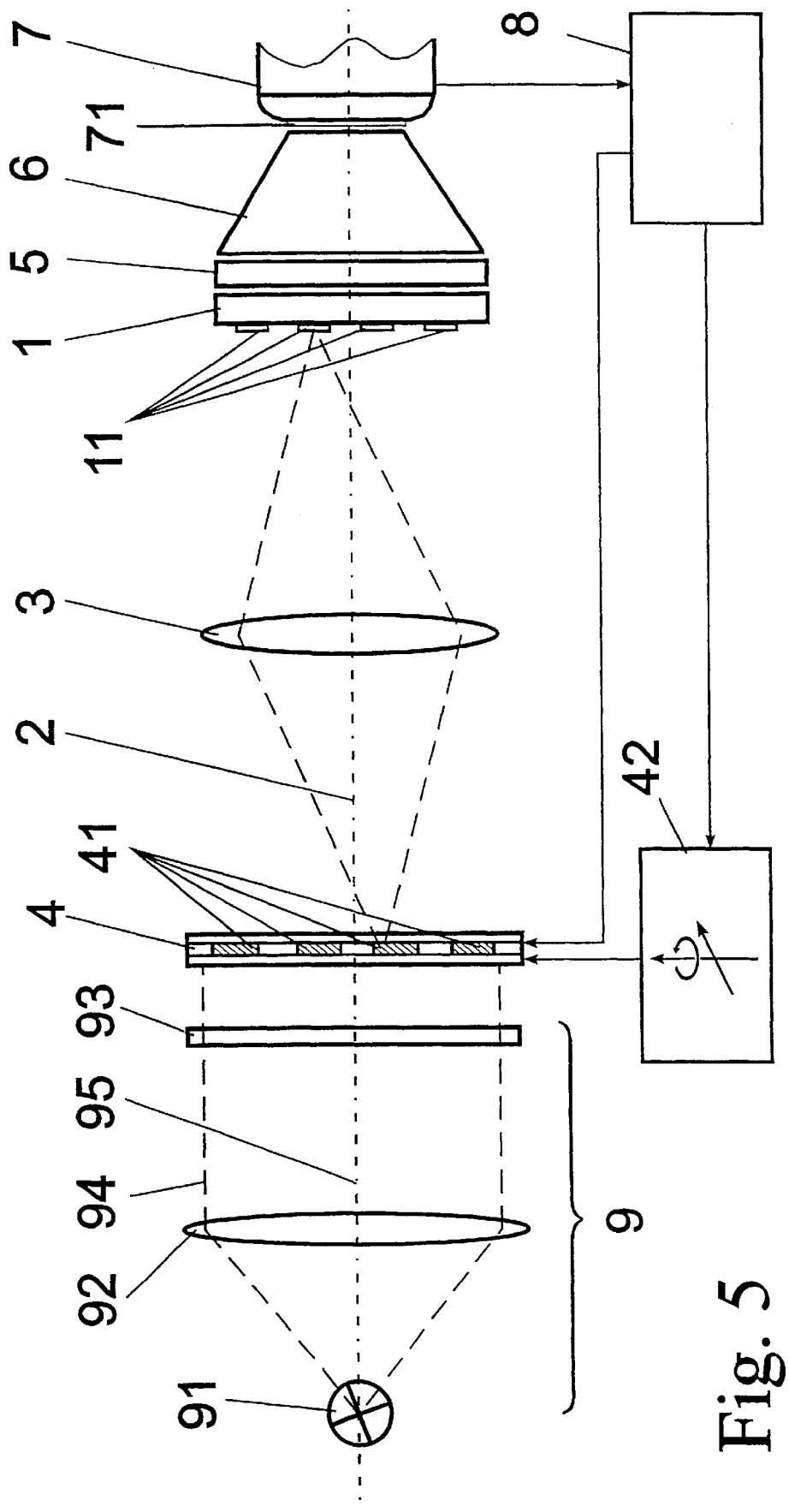
FIG. 5 shows an advantageous variant of the invention in which the transfer optical arrangement is arranged in the pencil of rays from the illumination unit, in a transmitted-light bright-field configuration.

FIGS. 3 to 5 below differ essentially in terms of the type of illumination used.

In FIG. 3, the illumination device 9 is arranged in a transmitted-light bright-field configuration, that is to say the optical axes 2 and 95 coincide. The substrate pixels 11 are illuminated uniformly through the substrate 1. As already described with respect to FIGS. 1 and 2, the substrate pixels 11 are imaged on specific regions of pixels 41 of the LC matrix 4. Depending on the control of the transparency of the matrix pixels 41, the fluorescent radiation is switched through by the evaluation regime of specific substrate pixels 11 and converted optoelectronically.

For a technical design of the arrangement according to the invention which is "robust" with regard to environmental influences (vibrations, large temperature range or the like, as are found e.g. in vehicles), it is expedient to carry out an autocalibration of the imaging of the substrate plane in the plane of the LC matrix 4 at specific (relatively long) time intervals or after severe loading. Such a precaution is indicated in the form of the actuating unit 42, which renders the LC matrix 4 adjustable with regard to its position in two orthogonal directions with respect to the optical axis 2 and also at least about one of these axial directions. This can expediently be realized by a regulating circuit, in the case of which the actuating element 42 is an x,y,Φ piezoelectric actuator which moves the LC matrix 4 until a regulating signal assumes an extreme value. This regulating signal can be formed as follows: at least three pixels 41 of the substrate 1 are designed as calibration pixels and are arranged in the plane of the substrate 1 (either as an integral part of each substrate, which is expedient principally in the case of biochips, or as part of the substrate mount), conjugate pixels 41 of the LC matrix 4 exist with respect to these calibration pixels and are all switched to be transparent during the adjustment operation (all other matrix pixels 41 being closed) and an actuating movement of the matrix 4 is carried out by means of the actuating element 42 until the receiver signal becomes the absolute maximum.

The matrix 4, the actuating element 42 and the receiver 7 are electrically connected to the control and evaluation unit 8, which may contain the electronics for driving these components, an A/D converter, a PC or a memory for pattern libraries. The task of this control and evaluation unit 8 is to realize measured-value acceptance synchronized with the driving of the matrix pixels 41 (and also of the actuating element 42 in the case of autocalibration), if appropriate to store these measured values and subject them to software evaluation. It may also be the task of this evaluation unit 8 to calibrate the accepted measured values with values that have been determined and stored before the actual measurement (examples of said values being extraneous light distributions in the optical arrangement, residual fluorescence of the substrate 1, dark current of the receiver 7, homogeneity distribution of the excitation radiation in the substrate 1, etc.).

For certain objectives, it may be expedient to switch relatively large numbers of pixels of the LC matrix 4 simultaneously in order e.g. to write stored radiation distributions of biochip images from a catalog and/or their negative image into the LC matrix 4.

Other configurations of the arrangement according to the invention which are favorable depending on the concrete objective may be obtained for example by omitting the mirror 96 from FIG. 2 for the processing of nontransparent substrates 1 and providing the elements 91 to 93 at the location of said mirror, thereby realizing reflected-light dark-field illumination, as illustrated in FIG. 4. The structure and the method of operation correspond, for the rest, to those of FIG. 2.

FIG. 5 contains a transmitted-light bright-field configuration with the same structure of the illumination device 9 as in FIG. 3. In this case, the special feature consists in the fact that the transfer optical arrangement comprising the objective 3 and the LC matrix 4 are arranged upstream of the substrate 1 and the substrate is positioned directly in front of the receiver 7, where the LC matrix 4 was located in each of the previous figures. The method of operation of the arrangement differs, then, by the fact that in this variant individual substrate pixels 11 of the substrate 1 are illuminated only selectively by means of the LC matrix 4 and thus, unlike before, the entire substrate 1 is not illuminated. The result on the receiver 7 remains the same, however, as that described for the previous figures.

Figure 6:
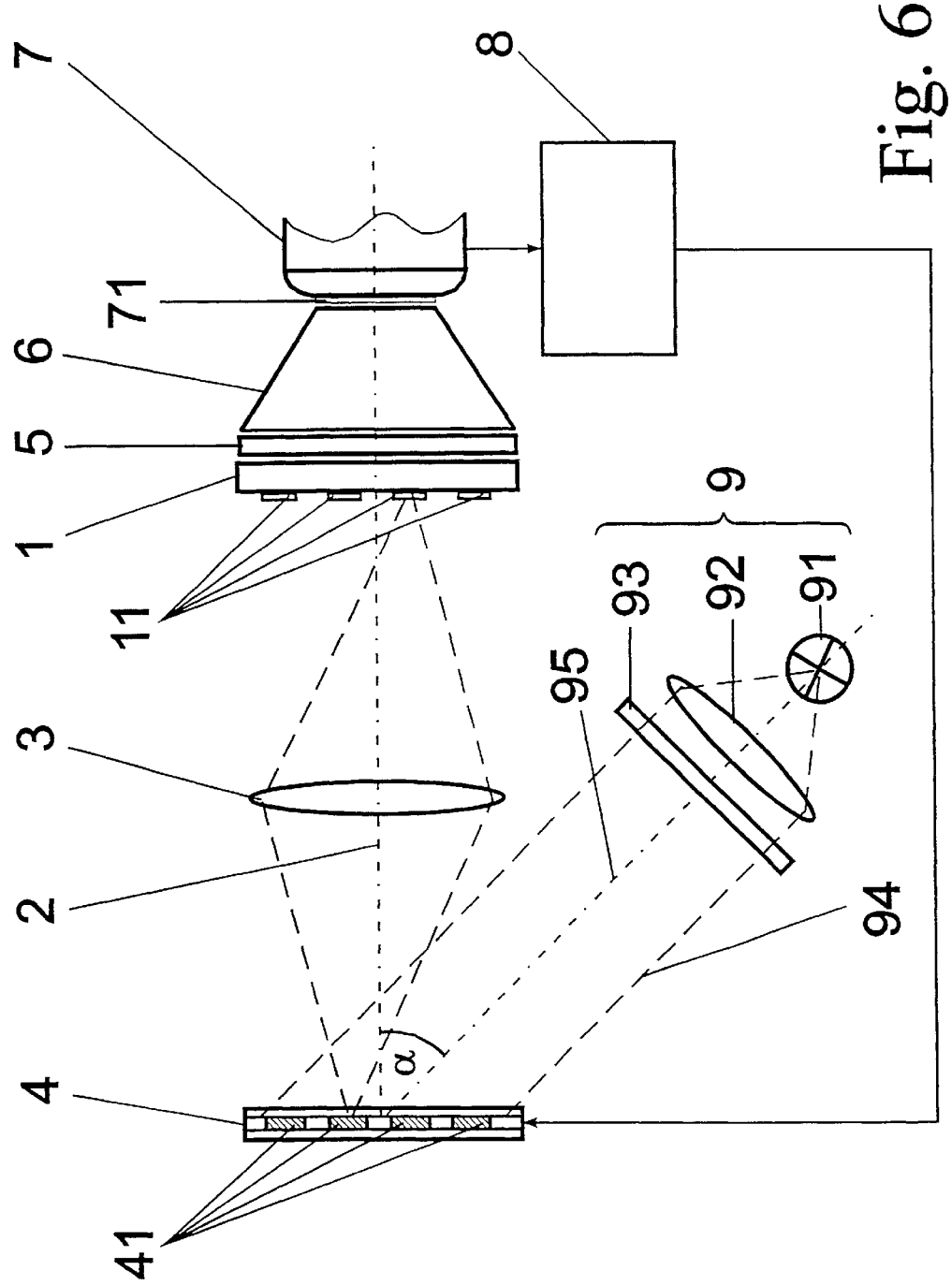
FIG. 6 shows a modified variant of the configuration in accordance with FIG. 5 in a reflected-light dark-field configuration.

FIG. 6 contains the same arrangement of LC matrix 4, objective 3 and substrate 1 as in FIG. 5, but with reflected-light dark-field illumination. The illumination device 9 with the known elements 91, 92 and 93 is now directed at an angle a to the optical axis 2 at that side of the LC matrix 4 which faces the receiver 7. The special feature of the LC matrix 4 in this case resides in the fact that the reflectivity of its matrix pixels 41 must be able to be controlled with high contrast. All other assignments of the elements of the arrangement are maintained as before.

Figure 10:
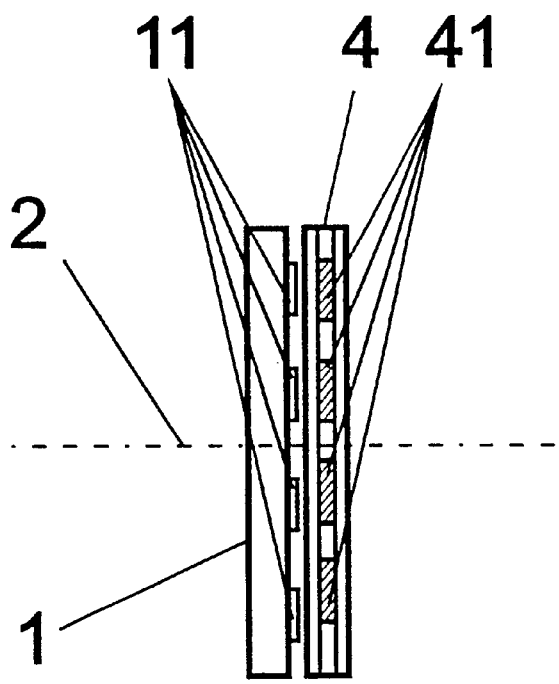
FIG. 10 shows a particularly compact design of the transfer optical arrangement by a quasi-contact of the electrooptical matrix with the substrate as direct imaging.
Figure 11:
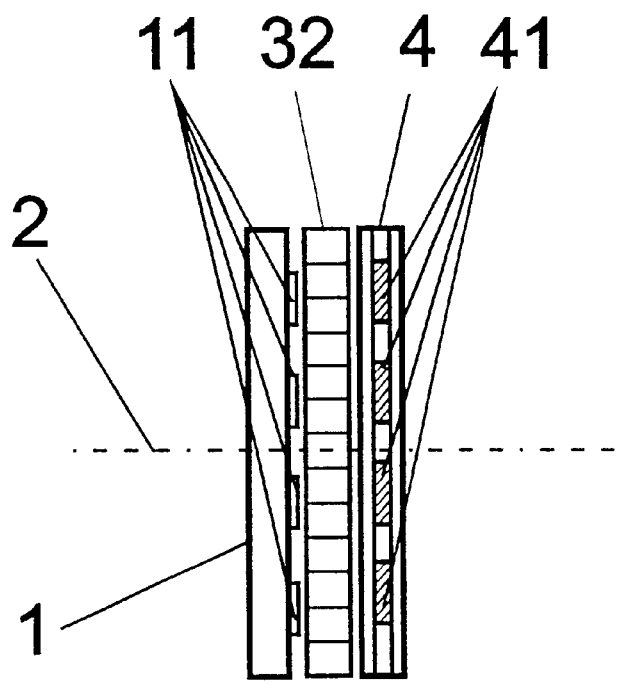
FIG. 11 shows a further compact configuration of the transfer optical arrangement, comprising fiber plate and electrooptical matrix.

In order to obtain a particularly compact design of the arrangement according to the invention, the substrate 2 and the LC matrix 4 may also be arranged in "quasi-contact". This variant is shown as a detail in FIG. 10. A design which better separates or guides the fluorescent light emerging from the substrate pixels 11 on all sides is illustrated in FIG. 11. In this case a fiber plate 32 is inserted between the substrate 2 and the LC matrix 4, which fiber plate couples the two elements to one another and thus guides the fluorescent light onto the matrix pixels 41 with few losses.

While the foregoing description and drawings represent the preferred embodiments of the present invention, it will be obvious to those skilled in the art that various changes and modifications may be made therein without departing from the true spirit and scope of the present invention.

List of Reference Symbols Used

1 Substrate
11 Substrate pixel
2 Optical axis
3 Optically imaging system (objective)
31 Individual lenses of a lens array
4 Electrooptical matrix (LC matrix)
41 Matrix pixel
42 Actuating unit
5 Rejection filter
6 Radiation-concentrating optical elements
61 Converging lens
17 Receiver (SEM)
71 Active light-sensitive area (entry window) of the SEM
8 Evaluation unit
9 Illumination device
91 Light source
92 Condenser optical arrangement
93 Excitation filter
94 Parallel (collimated) pencil of rays
95 Optical axis of the illumination device
96 Mirror
α Angle between the optical axes

What is claimed is:

1. An arrangement for optical reading out the information from a matrix-type substrate having a multiplicity of individual samples, which represent metrically ordered pixels on the substrate and emit a radiation which is characteristically influenced by an individual sample substance, comprising:
   a receiver;
   a transfer optical arrangement for separately transferring the radiation emitted by individual substrate pixels to said receiver;
   said receiver being a single receiver which has a high sensitivity and a uniform receiver area and being able to take up the radiation from each substrate pixel;
   said transfer optical arrangement having an electro-optical matrix, which has the function of a variable light valve for separately transferring radiation from each substrate pixel to the receiver and being arranged in such a way that each substrate pixel being imaged in an optical one-to-one-assigned manner to a matrix region comprising at least one matrix pixel; and
   said matrix being able to be driven in such a way that matrix regions of such a size which allow the feeding of radiation from only one substrate pixel to the receiver can be switched separately, radiation quantities from in each case at least one substrate pixel successively impinging on the receiver over a suitable chosen time interval, so that it is possible to evaluate a series of measured radiation quantities from selected sequences of substrate pixels at the output of the receiver.

2. The arrangement as claimed in claim 1, wherein intensive illumination is provided for generating the radiation which is characteristically influenced by the substrate pixels.

3. The arrangement as claimed in claim 2, wherein the radiation which is characteristically influenced by the substrate pixels is a luminescent radiation generated by the illumination.

4. The arrangement as claimed in claim 3, wherein the radiation which is characteristically influenced by the substrate pixels is a fluorescent radiation.

5. The arrangement as claimed in claim 2, wherein, for generating the radiation which is characteristically influenced by the substrate pixels, provision is made of illumination for reading out the transmissivity or reflectivity of the substrate pixels.

6. The arrangement as claimed in claim 1, wherein, for generating the characteristically influenced radiation from the substrate pixels, provision is made of an illumination device having a parallel pencil of rays which, with optical components arranged downstream being taken into account, is suitable for the large-area uniform illumination of all the substrate pixels.

7. The arrangement as claimed in claim 1, wherein for generating the radiation which is characteristically influenced by the substrate pixels, provision is made of a chemical reaction by contact of the substrate pixels with a surrounding medium.

8. The arrangement as claimed in claim 7, wherein for generating the radiation which is characteristically influenced by the substrate pixels, contact of the substrate pixels with a liquid is provided.

9. The arrangement as claimed in claim 1, wherein the transfer optical arrangement is arranged between the substrate and the receiver, it being possible for the characteristic radiation from each substrate pixel to be detected individually on the receiver by assigned matrix regions of the electrooptical matrix being switched to be transparent.

10. The arrangement as claimed in claim 9, wherein each substrate pixel is imaged by the imaging optical system on a respective matrix pixel, it being possible in each case for the characteristic radiation from the assigned substrate pixel to be detected on the receiver by an arbitrary matrix pixel being switched to be transparent.

11. The arrangement as claimed in claim 9, wherein each substrate pixel is imaged by means of the imaging optical system on a respective group of matrix pixels which is geometrically similar to the substrate pixels, it being possible in each case for the characteristic radiation from the assigned substrate pixel to be detected on the receiver by such a group of matrix pixels being switched to be transparent.

12. The arrangement as claimed in claim 6, wherein the transfer optical arrangement is arranged upstream of the substrate in the parallel pencil of rays from the illumination device, the matrix pixels of the electrooptical matrix being illuminated uniformly by the illumination device and it being possible for the substrate pixels to be illuminated individually with the illumination light by activation of defined matrix regions of the electrooptical matrix, and the substrate being connected to the receiver in such a way that the radiation coming from any arbitrary substrate pixel can be taken up by the receiver essentially without any losses.

13. The arrangement as claimed in claim 12, wherein a respective matrix pixel is imaged by the imaging optical system on a substrate pixel, the assigned substrate pixel, for generating the characteristic radiation, being illuminated by activation of the respective matrix pixel.

14. The arrangement as claimed in claim 12, wherein a respective group of matrix pixels which is geometrically similar to the substrate pixels is imaged by the imaging optical system on a substrate pixel, the assigned substrate pixel, for generating the characteristic radiation, being illuminated by activation of the respective group of matrix pixels.

15. The arrangement as claimed in claim 9, wherein the electrooptical matrix is a liquid crystal matrix having high contrast and short switching times.

16. The arrangement as claimed in claim 15, wherein the electrooptical matrix is a ferroelectric liquid crystal matrix having bistable switching states.

17. The arrangement as claimed in claim 9, wherein the imaging optical system is a fiber optical arrangement preferably a fiber plate, there being a light-guiding connection between the substrate pixels and the assigned matrix pixels as a result of direct contact of the fiber optical arrangement with the substrate, on the one hand, and the electrooptical matrix, on the other hand.

18. The arrangement as claimed in claim 1, wherein for the purpose of optical data reduction, the electrooptical matrix can be activated in suitably chosen matrix regions, with the result that radiation quantities from a plurality of selected substrate pixels can be detected simultaneously on the receiver and are combined to form a receiver measured value, it being possible to compare measured values that have been obtained in this way with radiation values of specimen substrates which have been measured under the same preconditions.

19. The arrangement as claimed in claim 3, wherein the illumination device contains an incoherent light source and a narrowband excitation filter tuned to the excitation wavelength of the luminescent material of the substrate pixels.

20. The arrangement as claimed in claim 19, wherein the excitation filter can be exchanged for adaptation to different luminescent materials of the substrate pixels.

21. The arrangement as claimed in claim 19, wherein the illumination device has a relatively broadband powerful light source.

22. The arrangement as claimed in claim 21, wherein the light source is a halogen lamp.

23. The arrangement as claimed in claim 21, wherein the light source is a powerful light-emitting diode.

24. The arrangement as claimed in claim 3, wherein the illumination device contains a coherent light source which is provided with beam-expanding optics and, with regard to the wavelength, is adapted to the excitation wavelength of the luminescent materials of the substrate pixels.

25. The arrangement as claimed in claim 6, wherein the illumination device is designed in a transmitted-light bright-field configuration.

26. The arrangement as claimed in claim 6, wherein the illumination device is designed in a transmitted-light dark-field configuration.

27. The arrangement as claimed in claim 26, wherein a mirror is arranged in the light path of the parallel pencil of rays which transmissively passes through the substrate, the reflected light of which mirror is provided as an additional reflected-light dark-field light pencil with regard to the substrate.

28. The arrangement as claimed in claim 6, wherein the illumination device is designed in a reflected-light dark-field configuration.

29. The arrangement as claimed in claim 12, wherein the illumination device is designed in a reflected-light dark-field configuration, the activation of the matrix pixels resulting in a change to their reflectivity.

30. The arrangement as claimed in claim 3, wherein a rejection filter for eliminating the illumination light is present in the beam path upstream of the receiver.

31. The arrangement as claimed in claim 1, wherein the receiver is a secondary electron multiplier.

32. The arrangement as claimed in claim 1, wherein optical elements which concentrate the characteristically influenced radiation from all the substrate pixels onto the active light-sensitive area of the receiver are provided upstream of the receiver.

33. The arrangement as claimed in claim 32, wherein a converging optical arrangement is arranged upstream of the receiver and is provided for the purpose of imaging the characteristically influenced radiation from each substrate pixel on the active light-sensitive area of the receiver.

34. The arrangement as claimed in claim 32, wherein a radiation-concentrating element is arranged upstream of the receiver.

35. The arrangement as claimed in claim 34, wherein the radiation-concentrating element is a cross-section converter, in the form of a truncated glass cone.

36. The arrangement as claimed in claim 1, wherein an electromechanical actuating unit is provided for regularly readjusting the transfer optical arrangement relative to the substrate.

37. The arrangement as claimed in claim 36, wherein the substrate can be displaced, by the actuating unit, relative to the entire transfer optical arrangement in two directions of an orthogonal plane with respect to the optical axis and can be rotated at least about one axis.

38. The arrangement as claimed in claim 36, wherein the electrooptical matrix can be displaced, by the actuating unit, relative to the imaging optical system and the substrate in two directions of an orthogonal plane with respect to the optical axis and can be rotated at least about one axis.

39. The arrangement as claimed in claim 37 or 38, wherein the mechanical actuating unit that is present is a piezoelectric x, y, $\Phi$ actuator whose driving is oriented, by regulation, to maximizing the luminescent light efficiency for defined substrate pixels, in particular edge pixels, of a specimen substrate.

* * * * *